United States Patent [19]

Haslam, II et al.

[11] Patent Number: 5,413,611
[45] Date of Patent: May 9, 1995

[54] COMPUTERIZED ELECTRONIC PROSTHESIS APPARATUS AND METHOD

[75] Inventors: Thomas P. Haslam, II; Michael E. Tompkins, both of Sugar Land, Tex.

[73] Assignee: MCP Services, Inc., Houston, Tex.

[21] Appl. No.: 915,618

[22] Filed: Jul. 21, 1992

[51] Int. Cl.⁶ ............................ A61F 2/72; A61F 2/54
[52] U.S. Cl. ......................................... 623/25; 623/24; 623/57
[58] Field of Search ........................ 623/24, 25, 57, 64

[56] References Cited

U.S. PATENT DOCUMENTS

| | | | |
|---|---|---|---|
| 3,418,662 | 12/1968 | Bottomley et al. | 623/25 |
| 3,423,765 | 1/1969 | Salisbury | 623/24 |
| 3,820,168 | 6/1974 | Horvath | 623/24 |
| 4,302,138 | 11/1981 | Zarudiansky | 414/5 |
| 4,650,492 | 3/1987 | Barkhordar et al. | 623/24 |
| 4,770,662 | 9/1988 | Gianpapa | 623/24 |
| 4,808,187 | 2/1989 | Patterson et al. | 623/25 |
| 5,252,102 | 10/1993 | Singer et al. | 623/24 |

FOREIGN PATENT DOCUMENTS

| | | | |
|---|---|---|---|
| 2518854 | 12/1975 | Germany | 623/25 |
| 1197155 | 7/1970 | United Kingdom | 623/25 |
| 0278023 | 8/1970 | U.S.S.R. | 623/25 |

OTHER PUBLICATIONS

Salisbury et al., "A Mechanical Hand with Automatic Proportional Control of Prehension", Med & biol Engng. J, pp. 505-511 (1967).

Shannon, "A Comparison of Alternative Means of Providing Sensory Feedback on Upper Limb Prostheses", Med. & biol. Engng, May 1976.

Primary Examiner—David H. Willse
Attorney, Agent, or Firm—Bernard A. Reiter & Associates

[57] ABSTRACT

A computerized electronic hand prosthesis apparatus and method utilizing input, feedback, control, and operating systems configurable to provide precise control and gripping forces corresponding to the particular capabilities and requirements of an individual wearer. An articulated prosthesis is capable of exerting a mechanical gripping force and contains a programmable microcomputer. Electrodes on the prosthesis contact muscles of the remnant portion of a limb and produce an electric command signal responsive to the myoelectric signal created by the wearer contracting and relaxing the muscles in the remnant portion. A drive motor in the prosthesis causes the prosthesis to exert a mechanical gripping force responsive and proportional to the electric command signal. Force sensors in the digits of the prosthesis detect the force exerted and produce an electric sensor signal responsive and proportional thereto. A motor driven vibratory device on the prosthesis engages the remnant portion of the limb adjacent sensory nerves and produces a feedback signal perceptible to the wearer which changes in vibratory pattern and amplitude at various selective grip forces. A communication port on the prosthesis is releasably connected to peripheral devices for exchanging data, diagnosing, correcting, or setting the operational parameters of the prosthesis. The electrodes, drive motor, force sensors, vibratory device, and communication port are controlled by the microcomputer.

26 Claims, 5 Drawing Sheets

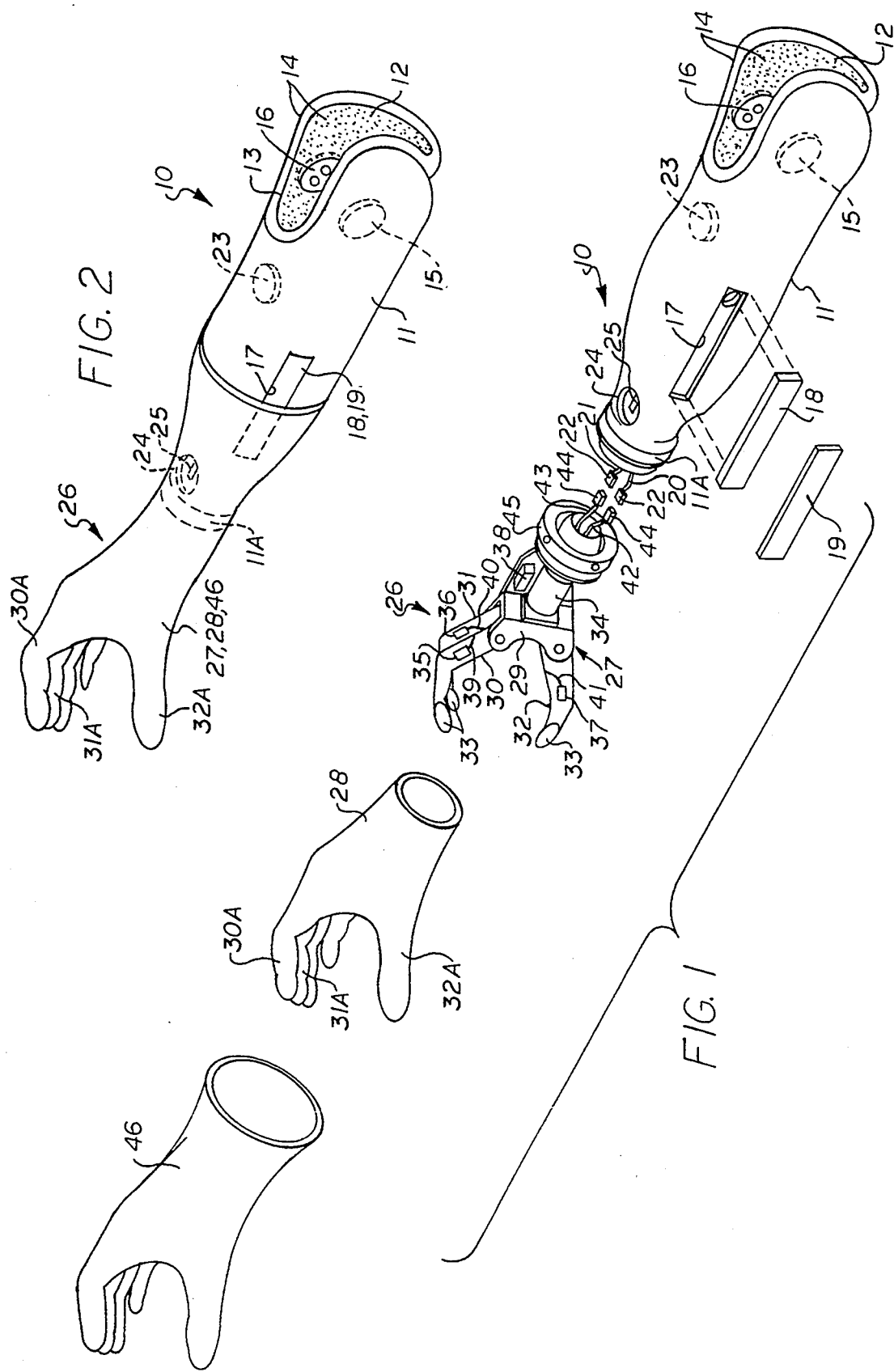

HAND MOTOR ON/OFF CONTROL

ELECTRODE LOWER THRESHOLD

ELECTRODE UPPER LIMIT

COMPUTERIZED ELECTRONIC PROSTHESIS APPARATUS AND METHOD

BACKGROUND OF THE INVENTION

1. Field of the Invention

This invention relates generally to prosthetic apparatus and methods, and more particularly to a computerized electronic hand prosthesis apparatus and method utilizing configurable input, feedback, control, and operating systems to transmit feedback signals representing the gripping force back to the wearer in the form of vibratory stimuli which changes in vibratory pattern and amplitude at selective grip forces and allow precise positioning and gripping force control for a specific wearer.

2. Brief Description of the Prior Art

Although the mechanical hand is more acceptable than other prosthetic terminal devices, the problems associated with using a conventional mechanical hand prosthesis limits its usefulness and ultimately affects the wearer's acceptance of the prosthesis.

A person with a conventional mechanical hand prosthesis has the ability to control the grip of an object based only on visual or aural feedback. This is a problem because the wearer must discern the amount of pressure to apply to objects based on the deflection of a surface, the sound of the hand drive motor, or guessing on trial and error. If the grip is too tight, the object may be crushed or break, or, if too light, the object may be dropped. If the wearer is distracted or forgets that the hand is still holding the object, the lack of feedback could create a dangerous or embarrassing situation.

Most conventional electric control systems that drive the mechanical hand are simple designs which allow two conditions, either full speed or off. This makes it difficult for the wearer to accurately position the hand which affects gripping ability.

Conzelman, Jr. et al, U.S. Pat. No. 2,656,545, discloses a prosthetic device having a sensory apparatus for transmitting to the wearer of the artificial device an indication of contact that is made by the artificial member. In one embodiment, a bladder on the end of the finger of the prosthesis is connected by a flexible tube to a second bladder held by a harness to a normally sensitive part of the skin of the stump of the amputee. In another embodiment, a switch on the end of the finger of the prosthesis closes an electrical circuit in response to finger tip pressure and a vibrator disc held by a harness to a normally sensitive part of the skin vibrates in intensity relative to the finger tip pressure.

Patterson et al, U.S. Pat. No. 4,808,187, discloses a tactile stimulus receptor for use with a myoelectric prosthesis having a piezoelectric transducer positioned on the gripping fingers of the prosthesis which senses pressure resulting from gripping and converts the sensed pressure into electrical signals proportional to the pressure to a hydraulic motor and cylinder which is connected by a tube to a pressurizable cuff mounted on the wearer's forearm. The cuff constricts the forearm upon increased pressurization and reduces constriction upon reduced pressurization.

Fletcher et al, U.S. Pat. No. 3,751,733, discloses a prosthetic device including a socket for mounting the frame of the device on the stump of the amputee. A piezoelectric transducer and a temperature transducer are provided in flexible digits of the hand for sensing pressure and temperature. The transducers detect tactile stimuli and are connected through a power circuit to a pair of solenoids and a resistance heating element supported by a strap buckled about the stump. Tactile stimuli detected at the sensing devices are reproduced and applied to the skin of the appendage as a pinching and heating or cooling sensation for stimulating sensory organs.

Barry, U.S. Pat. No. 4,571,750, discloses the use of acoustic signals generated by muscles during contraction to generate signals responsive to muscle activity. The invention relates to a complex method of analyzing a human body and controlling prosthetic devices which use acoustic signals obtained from skeletal muscles alone and in combination with myoelectric signals.

Barkhordar et al, U.S. Pat. No. 4,650,492, relates to an artificial hand that comprise a palm member and thumb and finger members movable by an actuator. A microphone is used to pick up pressure waves resulting from a stick/slip motion of the object being picked up along the surface of the hand.

Giampapa, U.S. Pat. No. 4,770,662, discloses sonic frequency generators in electrical communication with pressure transducers in the digits of an artificial hand. Output signals in the form of voltage and sonic frequency are transferred to a bone stump and transmitted to the brain via the spinal column.

The present invention is distinguished over the prior art in general, and these patents in particular by a computerized electronic hand prosthesis apparatus and method utilizing input, feedback, control, and operating systems configurable to provide precise control and gripping forces corresponding to the particular capabilities and requirements of an individual wearer. An articulated prosthesis capable of exerting a mechanical gripping force contains a programmable microcomputer. Electrodes on the prosthesis contact muscles of the remnant portion of a limb and produce an electric command signal responsive to the myoelectric signal created by the wearer contracting and relaxing the muscles in the remnant portion. A drive motor in the prosthesis causes the prosthesis to exert a mechanical gripping force responsive and proportional to the electric command signal. Force sensors in the digits of the prosthesis detect the force exerted and produce an electric sensor signal responsive and proportional thereto. A motor driven vibratory device on the prosthesis engages the remnant portion of the limb adjacent sensory nerves and produces a feedback signal perceptible to the wearer which changes in vibratory pattern and amplitude at various selective grip forces. A communication port on the prosthesis is releasably connected to peripheral devices for exchanging data, diagnosing, correcting, or setting the operational parameters of the prosthesis. The electrodes, drive motor, force sensors, vibratory device, and communication port are controlled by the microcomputer.

SUMMARY OF THE INVENTION

It is therefore an object of the present invention to provide a prosthetic apparatus and method utilizing configurable input, feedback, control, and operating systems to transmit feedback signals representing the gripping force back to the wearer to allow precise positioning and gripping force control corresponding to the particular capabilities and requirements of an individual wearer.

It is another object of the present invention to provide a prosthetic apparatus and method utilizing control by the wearer to exert mechanical forces in the prosthesis and sensors in the prosthesis to transmit feedback signals representing the exerted forces back to the wearer in the form of vibratory stimuli which change in vibratory pattern and amplitude at various selective grip forces corresponding to the particular capabilities and requirements of an individual wearer.

Another object of this invention to provide a computerized electronic hand prosthesis apparatus and method utilizing configurable input, feedback, control, and operating systems and control by the wearer to exert a mechanical grip force and grip sensors in the hand digits to transmit feedback signals representing the gripping force back to the wearer in the form of vibratory stimuli which change in vibratory pattern and amplitude at various selective grip forces corresponding to the particular capabilities and requirements of an individual wearer.

Another object of this invention is to provide an articulated prosthesis to be worn by a living being which contains a programmable microcomputer having a variety of operating programs in memory storage corresponding to the particular capabilities and requirements of the individual wearer.

Another object of this invention is to provide a computerized electronic prosthesis which is easily operated by the wearer contracting certain muscles of the remnant portion of their limb to produce a myoelectric signal and receiving a non-irritating feedback signal easily perceived by the wearer which is representative of the mechanical force exerted.

Another object of this invention is to provide a computerized electronic hand prosthesis having a communications port connected with the microcomputer for releasably connecting the prosthesis to peripheral devices for exchanging data, monitoring, diagnosing, adjusting, correcting, or setting the operational parameters of the prosthesis.

A further object of this invention is to provide a computerized electronic hand prosthesis which will automatically detect and compensate for loss of mechanical gripping force without any action on the part of the wearer.

A still further object of this invention is to provide a computerized electronic hand prosthesis which is cosmetically superior, lighter in weight, and stronger than conventional prosthetic devices.

Other objects of the invention will become apparent from time to time throughout the specification and claims as hereinafter related.

The above noted objects and other objects of the invention are accomplished by a computerized electronic hand prosthesis apparatus and method utilizing input, feedback, control, and operating systems configurable to provide precise control and gripping forces corresponding to the particular capabilities and requirements of an individual wearer. An articulated prosthesis capable of exerting a mechanical gripping force contains a programmable microcomputer. Electrodes on the prosthesis contact muscles of the remnant portion of a limb and produce an electric command signal responsive to the myoelectric signal created by the wearer contracting and relaxing the muscles in the remnant portion. A drive motor in the prosthesis causes the prosthesis to exert a mechanical gripping force responsive and proportional to the electric command signal. Force sensors in the digits of the prosthesis detect the force exerted and produce an electric sensor signal responsive and proportional thereto. A motor driven vibratory device on the prosthesis engages the remnant portion of the limb adjacent sensory nerves and produces a feedback signal perceptible to the wearer which changes in vibratory pattern and amplitude at various selective grip forces. A communication port on the prosthesis is releasably connected to peripheral devices for exchanging data, diagnosing, correcting, or setting the operational parameters of the prosthesis. The electrodes, drive motor, force sensors, vibratory device, and communication port are controlled by the microcomputer.

BRIEF DESCRIPTION OF THE DRAWINGS

FIG. 1 is an exploded isometric view of the components of the computerized electronic hand prosthesis apparatus in accordance with the present invention shown in an unassembled condition.

FIG. 2 is an isometric view of the basic computerized electronic hand prosthesis apparatus in the assembled condition.

DESCRIPTION OF THE PREFERRED EMBODIMENT

Figure 3:
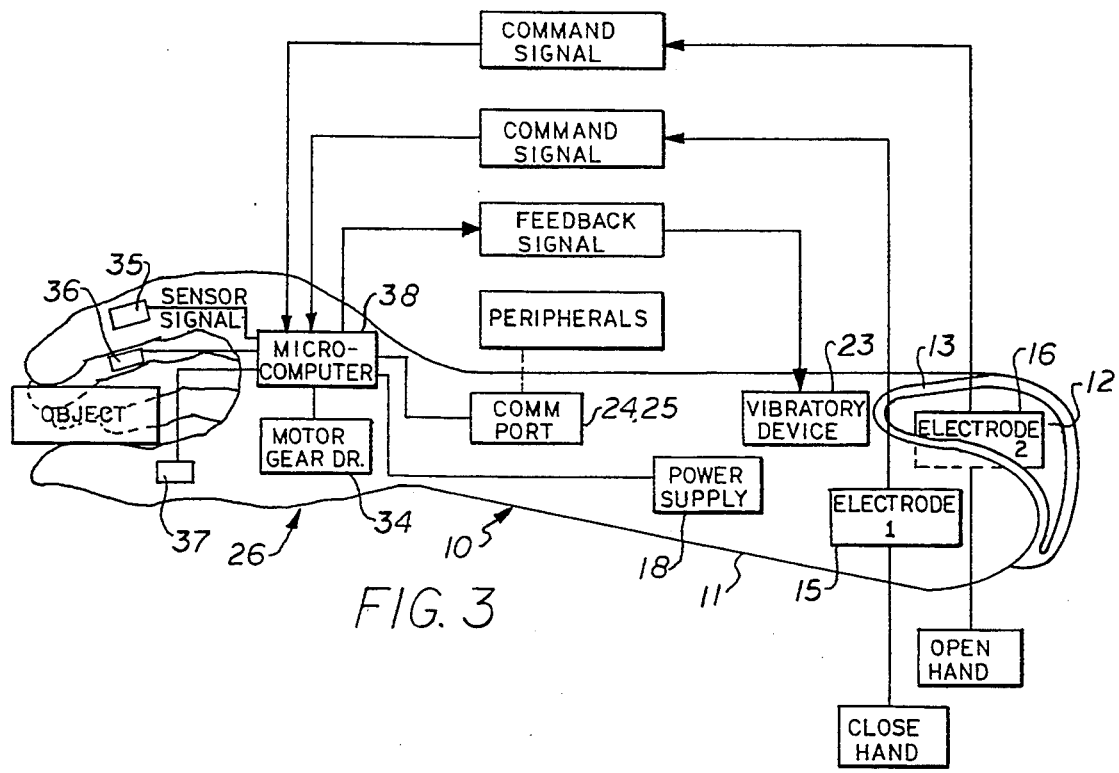
FIG. 3 is a side elevation of the hand prosthesis with the basic components illustrated schematically in block diagram.

Referring to the drawings by numerals of reference, there is shown in FIGS. 1, 2 and 3, a preferred computerized electronic hand prosthesis apparatus 10. The components are shown in the unassembled condition in FIG. 1, and in the assembled condition in FIG. 2.

Unlike prior art two-piece lower arm prosthetic devices, the present invention may utilize a one-piece molded forearm member 11. The forearm member 11 is made by casting a mold of the stump of the patient and molding the rear or upper end of forearm member to conform to the remnant limb of the particular patient to be fitted and the lower portion of the forearm member to closely resemble the size and shape of the remaining or natural forearm. The upper end of the forearm 11 is thus fashioned into a custom sleeve or socket 12 and has a molded longitudinal slot 13 extending downwardly a short distance from the upper or socket end. Suitable padding material 14 is provided on the interior surface and surrounding edges of the socket portion 12. In use, the forearm 11 is removably attached to the wearer by pulling the remnant limb into the socket 12. The slotted upper portion of the socket 12 expands over the elbow, clasping the forearm member into place. The forearm is self-suspending and in most applications requires no straps or cables.

While a forearm member is described in the preferred embodiment, it should be understood that in some applications, a complete upper and lower arm member may be used and in other applications the hand prosthesis and accompanying electronic components (described below) may be attached to the wrist area of the remnant limb. The present invention may also be incorporated into other limbs, such as the upper or lower leg.

In the following discussion, the term "electrode" is used to describe the wearer input device, however, it should be understood that various input devices may be used, such as; myoelectric electrodes, sense resistors, variable resistors, pull switches, touch capacitance switches or plates, rocker switches, strain gauges, and similar devices. A dual electrode system is described as an example, wherein one electrode controls opening of the hand and the other electrode controls closing of the hand, however, it should be understood that a single electrode may also be used to either open or close the hand. The electrode type may be analog, digital, proportional, or linear.

The forearm member 11 is formed of lightweight material and is substantially hollow. A pair of electrodes 15 and 16 are mounted in the interior surface of the forearm 11. One electrode 15 is used for closing the hand and the other electrode 16 is used for opening the hand. The position of the electrodes 15 and 16 within the forearm 11 corresponds to the strong muscle groups in the stump of the limb covered by the socket end of the forearm and are activated by the wearer flexing a muscle. Muscle contractions on the medial side of the remnant limb close the hand and muscle contractions on the lateral side open the hand. As a muscle contracts it gives of an electrical stimulus which is received and amplified by the electrodes 15 and 16.

The exterior surface of the forearm member 11 has a cavity or recess 17 formed therein which removably receives a battery 18. In the preferred embodiment, the battery recess 17 is configured such that the battery 18 can be snapped into the recess 17 and enclosed by a removable cosmetic cover 19.

The electronic system is designed to operate over a full power and temperature range with an input voltage range of 4.5 to 7.5 volts without external regulators. A 6 volt nickel cadmium battery is preferred. Power supplied to components not operable in this range are pre-regulated to their proper voltage range through voltage regulators.

The electronic system does not require an on/off switch, but rather has an automatic "sleep mode" which reduces power 95% if the wearer does not make an active electrode signal for a variable period of time. Thus, the present system is a "warm" start rather than a "cold" start, and will be triggered upon a valid electrode input.

The battery 18 is electrically coupled to the electrodes 15 and 16 and a microcomputer (described below) through a wiring harness disposed within the interior of the forearm 11. A pair of insulated flexible leads 20 and 21 connected to the electrodes 15 and 16 extend through the wrist portion 11A of the forearm 11 and their outer ends are provided with modular plug connectors 22.

A motor driven vibratory device 23 is mounted in the exterior surface of the forearm member 11 near upper end for firm engagement with the skin of the remnant portion of the limb inside the socket end 12 of the forearm member. The motor driven vibratory device 23 converts electrical impulses into vibrations which are transmitted directly to the remnant portion of the limb for nerve stimulation as "feedback" signals to the wearer (described hereinafter). The motor driven vibratory device 23 is connected to a microcomputer (described below) through the leads 20 and 21 and modular connectors 22. The motor driven vibratory device 23 electrically and mechanically provides more vibration for the amount of power available than audio loud speakers or piezoelectric crystal devices. Preferably, the vibratory device 23 runs in the range of 30 cycles per second.

A communication port 24 is recessed in the exterior surface of the forearm member 11 near the wrist portion 11A and has a communication connector 25 mounted therein for releasably connecting the prosthetic hand to peripheral equipment. The communications connector 25 is joined by leads 20 and 21 and modular connectors 22 to the microcomputer housed in the prosthetic hand (described below). The wrist end 11A of the forearm member 11 is adapted to be connected to an electro-mechanical hand assembly 26. The communication port 24 allows the microcomputer housed in the hand to be connected to peripheral equipment, such as a modem, personal computer, or other equipment for exchange of data, and monitoring, diagnosing, adjusting, or correcting the operational parameters of the hand (described hereinafter).

It should be understood that the mechanical hand depicted in the drawings is for exemplary purposes only and that other types of mechanical hands may be used. Also, in some applications, a transmission may be incorporated into the gear mechanism and in other applications the drive motor may be connected directly to the movable fingers (conventional in the art).

An electro-mechanical hand frame 27 is mounted within a molded hand frame cover 28 which is configured to closely resemble the hand of the wearer in shape and size and substantially covers the hand frame 27. The hand frame 27 has a yoke portion 29 with an index finger support 30, a middle finger support 31, and a thumb support 32, each pivotally mounted on the yoke portion at their rearward ends. Resilient pads 33 are mounted on the tips of the support members. The hand frame 27, finger supports 30, 31, and thumb support 32 are formed of lightweight rigid material, such as aluminum. The supports 30, 31, and 32 are slightly curved and are received in the index finger 30A, middle finger 31A, and thumb 32A, respectively, of the molded hand frame cover 28. The index finger 30A, middle finger 31A, and thumb 32A, of the molded hand frame cover 28 are articulated or flexible to be moved by the respective enclosed support members 30, 31, and 32.

The supports 30, 31, and 32 are connected through gears (not shown) to an electric D.C drive motor 34 mounted on the hand frame 27 and pivot between a predetermined open position and a closed position where the distal ends, or tips, of the index finger 30A, middle finger 31A, and thumb 32A, of the molded hand frame cover 28 are brought together in a pinching mode.

The electric D.C. drive motor is driven by a series of on/off pulses, utilizing "Pulse Width Modulation" (PWM), described hereinafter, which allows more precise control over the speed and torque of the motor than conventional linear analog approaches. The frequency of the pulses and the voltage applied to the motor remain constant, however, the duty cycle ("on" to "off" ratio) of the "on" time may be varied. For example, if the motor is driven with 6 volts at a 50% duty cycle this is the same as applying 3 volts of DC to the motor.

Strain gauge elements 35, 36, and 37 are mounted on the rigid supports 30, 31, and 32, respectively. As the hand closes and touches an object, compression stress forces will be exerted on the surfaces of the finger and thumb supports 30, 31, and 32. The strain gauge elements 35, 36, and 37 sense the amount of stress in the finger and thumb supports and convert it to electrical signals. The electrical "sensor" signal created by the hand should operate based on input from the wearer's electrodes. Variable data affecting the operation from wearer to wearer is stored EEPROM memory. The microcomputer is a substantially self-contained system with as many of the required system components embedded as possible to eliminate external components.

The microcomputer 38 sends and receives signals and controls the power to drive the hand mechanisms. The electrical "sensor" signal from the strain gauges 35, 36, and 37 is amplified to a level which the microcomputer can use and the microcomputer converts it through an analog/digital converter to digital numbers which are stored in the microcomputer memory and used in the programs to calculate feedback, starting and stopping the motor, changing speeds etc. Preferably all the wiring connections go through the microcomputer board (electrodes, motor, vibratory feedback, strain gauges, etc.). In some applications the microcomputer board may be mounted in or on the forearm member 11.

A wrist connection 45 at the rearward end of the hand frame 27 extends outwardly from the rear or wrist portion of the molded hand frame cover 28 to be connected to the wrist portion 11A of the forearm 11. The modular plug connectors 22 and 44 are connected together and the hand frame 27 and surrounding molded hand frame cover 28 assembled thereon is joined by the wrist connection 45 to the wrist portion 11A of the forearm member 11. The molded hand frame cover 28, wrist connection 45, and lower portion of the forearm 11 is covered by an elastomeric flexible skin-like glove 45 for cosmetic purposes.

Having thus described the major mechanical components of the present invention, a brief overview of the configurable features, variables, parameters, and software programs which can be changed to configure the microcomputer to provide maximum hand control for a specific wearer and provide maximum wearer adaptation will be described followed by a detailed description of the operation of the system.

CONFIGURATION

Referring now to FIGS. 4, 5, 6, 7, and 8, the following paragraphs describe a number of variables, parameters, and software programs which can be changed to configure the microcomputer for hand control for a specific wearer to provide maximum wearer adaptation.

"MAXIMUM CLOSE SPEED" is a variable stored in memory that will limit the maximum speed that the motor can close the hand. This allows the hand closing speed to be preset to anywhere between 30% and 100% of the normal maximum speed with maximum input from the "close" electrode.

"MAXIMUM OPEN SPEED" is a variable stored in memory that will limit the maximum speed that the motor can open the hand. This allows the hand opening speed to be preset to anywhere between 30% and 100% of the normal maximum speed with maximum input from the "open" electrode.

"PROPORTIONAL CONTROL" (FIG. 5) allows the rate at which the hand opens or closes to be changed linearly and directly proportional to the analog signal being produced by the electrode. Thus, the hand has the capability of digital proportional control operation. This mode is configurable and may be turned off for certain applications. When in the "off" mode, the system will default to the "On/Off Control" mode.

"ON/OFF CONTROL" (FIG. 6) is a mode of operation which may be varied to turn on the motor at the maximum speed when the myoelectric electrode signal goes above a preset threshold and turns the motor off when the signal goes below the threshold. For example, the adjustable threshold may be set at 40% with signals above the 40% threshold turning the motor on and signals below the 40% threshold turning the motor off.

The "POWER SUPPLY" is an electric D.C. drive motor driven by a series of on/off pulses, or "Pulse Width Modulation" (PWM) which allows more precise control over the speed and torque of the motor than conventional linear analog approaches. The frequency of the pulses and the voltage applied to the motor remain constant. The duty cycle ("on" to "off" ratio) of the "on" time is varied. For example, if the motor is driven with 6 volts at a 50% duty cycle this is the same as applying 3 volts of DC to the motor.

"SINGLE/DUAL ELECTRODES" is the capability of the system to operate with dual electrodes or with a single electrode. In the dual electrode mode, one electrode controls opening of the hand and the other electrode controls closing of the hand. The single electrode operation can be used to either open or close the hand depending upon the "Voluntary Open/Close" selection. The electrode type may be analog, digital, proportional, or linear. This variable is configurable and is stored in memory.

"VOLUNTARY OPEN/CLOSE" is a configuration parameter which works in conjunction with the "Single/Dual Electrode" mode to automatically close or open the hand, depending upon the selection, when the input signal is above or below the threshold.

"OPEN ELECTRODE LOWER THRESHOLD" (FIG. 7) sets the voltage point at which the microcomputer will acknowledge a valid "open" signal. This can be used to eliminate nuisance activations due to movement or environmental noise. This variable is configurable and stored in memory.

"CLOSE ELECTRODE LOWER THRESHOLD" (FIG. 7) sets the voltage point at which the microcomputer will acknowledge a valid "close" signal. This can be used to eliminate nuisance activations due to movement or environmental noise. This variable is configurable and stored in memory.

"OPEN ELECTRODE UPPER LIMIT" (FIG. 8) sets the gain for the "open" electrode. It can be adjusted to a lower value to allow a wearer with a weak input signal to still operate the hand and the maximum configured speed. The microcomputer scales the input signal between the lower threshold and the upper limit to 0% and 100%, respectively. This allows the system to be adjusted to match the requirements and capability of each wearer. This variable is configurable and stored in memory.

"CLOSE ELECTRODE UPPER LIMIT" (FIG. 8) sets the gain for the "close" electrode. It can be adjusted to a lower value to allow a wearer with a weak input signal to still operate the hand and the maximum configured speed. The microcomputer scales the input signal between the lower threshold and the upper limit to 0% and 100%, respectively. This allows the system to be adjusted to match the requirements and capability of each wearer. This variable is configurable and stored in memory.

"PINCH FORCE CONTROL" is a variable which determines how much force a hand can place on an object. Typically, the hand will be set from 5 pounds of force to a maximum of about 20 pounds of force. If the option is not required, the default will be the maximum value. The force is determined by combining the average force between the fingers and thumb with the stall current of the motor. This variable is configurable and stored in memory.

"VIBROUS FEEDBACK" is an stimuli signal generated by a vibratory device and transmitted directly to the remnant portion of the limb for nerve stimulation. The preferred vibratory device is a motor driven vibratory device running in the range of 30 cycles per second which provides maximum vibration for the amount of power that is available.

"VIBROUS PRESENTATION" is Pulse Code Modulation (PCM) with the main frequency set to allow maximum penetration through the skin to nerve endings and reduce the amount of power consumed. The modulation is proportional to the amount of force being applied by the hand. When the hand starts closing, regardless of where it is, a vibratory signal is immediately sent to the output vibratory device to give the wearer a reference point to start from (meaning no pressure). When the minimum force is detected on any of the fingers or thumb, another vibratory signal is sent to the output vibratory device. As the force increases, the strength of the signal increases. The feedback signal changes at various grip forces on the hand to a different vibratory pattern and amplitude which is configurable. The frequency, amplitude, and Pulse Code Modulation (PCM) are adjustable.

"VIBROUS FREQUENCY" is the frequency of the output feedback signal. It preferably is in the range of 30 cycles per second. Preliminary testing has shown that it is easier to detect minor changes on the skin surface by leaving the amplitude and base frequency at a fixed level and allow the microcomputer to vary the duty cycle of the frequency. This way the signal allows better sensitivity.

"FREQUENCY SHIFT OPTION" is a significant signal shift which occurs when force is detected on either of the fingers and the thumb indicating that the hand is gripping an object as opposed to just touching or pushing something with a finger. The range of the duty cycle will be proportional to the strength of the force applied to the fingers or thumb. The amount of frequency shift required is determined through testing. The sensor signals may be averaged or the dominant signal may be used.

"VIBROUS REMINDER" is a change in the vibrous feedback signal which prevents the wearer from becoming numb or ignoring the feedback signal and also reduces the amount of power consumed. A timer turns off the vibrous feedback signal shortly after the hand stops moving and then delays for several seconds before exerting the signal again. The time delay and the modulation of the frequency shall change each time so as not to become repetitive and predictable.

"AUTOMATIC SHUTOFF" is a variable stored in memory which protects the batteries from extreme discharge and possible cell voltage reversal. This variable is a predetermined voltage value at which the system will terminate operation.

"POWER DOWN OPERATION" is a standby mode of operation to minimize current consumption when there is no electrode signal or force sensor signal present. If there is no electrode signal present and no force on the fingers and thumb, the microcomputer will transfer into the standby mode where the current consumption of all electronics will be approximately 10% of normal. When an electrode signal is detected the system would immediately go back into full operation. A time delay may also be incorporated before switching into a sleep mode, but the transition from sleep to active will be immediate.

"GRIP LOSS DETECTION" is a software program which monitors when the hand is losing the grip on an object. When it is determined that the hand is losing its grip on the object the motor is activated to close the hand back to the original grip pressures. This action is independent of other wearer controlled functions. The "Grip Loss Detection" function is enabled or disabled by the use of a configuration jumper, or an EEPROM configuration bit.

"GRIP LOSS PROGRAM" is a software program which detects when there is a grip and records sensing pressures. The hand is said to have a grip on an object when there is force detected between the thumb and any other finger. When the hand is in the "close" mode the program detects when this condition occurs and stores the pressures in memory. When the hand is directed to stop closing, the final force values are recorded. The program then continuously monitors all finger pressures and looks for significant changes in force. If the force between the two fingers shifts to equal the same average value then there is no grip loss. If the force drops in the thumb and any one finger there is a grip loss. When the grip loss is detected the microcomputer immediately drives the motor in the "close" direction to re-establish the pressures originally set by the wearer. Variables available are the time delay for activation of the "Grip Loss Detector" program and the speed of the motor. Options include driving the motor at a speed proportional to the rate of the drop in force.

"MOTOR STALL DETECTION" is a software program which monitors the range of voltage generated by the motor during the "drive off" period, linearizes the data, and interprets the force exerted by the hand. The direct current motor used in the prosthetic hand is also a generator. Thus, if the shaft is turned it will generate a voltage. The motor will typically consume three to ten times its normal running current when it stalls. Since the motor is driven with a series of on/off pulses, or Pulse Width Modulation (PWM) (described below), the shaft is turned while applying voltage and the Back Electromotive Force (BEMF) of the motor during the drive "off" period can be monitored. If the generator voltage is near the drive voltage then the motor has very little load. If the generator voltage is near zero this means the motor has a large load or is stalled. The software monitors this range and by linearizing the data can interpret the force exerted by the hand.

"DIAGNOSTIC PROGRAM" is a software program which allows the system to perform internal diagnostics upon each "turn on", power connection, or through an external command via the communications port. A series of diagnostic tests check the status of the components and the memory devices. Any abnormalities are stored in the EEPROM for later retrieval, and may be signaled to the wearer through the vibratory device or other suitable method. Any non-fatal errors should be flagged and self corrected if possible.

A "COMMUNICATION PROGRAM" is a software program which allows the microcomputer in the hand to exchange data via the communication port between peripheral devices, such as a modem, computer, or other equipment for monitoring, diagnosing, adjusting, or correcting the operational parameters of the hand. A remote host system can be connected to the hand to read or write all unprotected data in the microcomputer controller. The preferred data transference is in ASCII format to allow easy interfacing.

A "SECURITY" program may also be stored in memory which will look for a series of events to occur. If it detects that certain events did not occur it will immediately execute a program which will write a erasure program into RAM and then proceed to erase all EPROM (set all bits to 0) and all EEPROM and write a security message in a specific memory location. Any unauthorized attempt to remove the memory contents and apply power will delete or corrupt the program. Unauthorized persons attempting to read, evaluate, or remove the system programs will only find the manufacturer's name, copyright notification, and a security message.

OPERATION

A myoelectric signal is created by the depolarization of the cell membrane of individual muscle fibers during contraction. The electric currents associated with this depolarization and the subsequent repolarization produce measurable electric potential differences in tissues some distance away. It is these electric potentials, rather than the transcellular potentials, which are generated by the wearer to be detected by the electrodes and used as the input signal to open or close the hand.

In the following discussion, a dual electrode mode is described as an example, wherein one electrode controls opening of the hand and the other electrode controls closing of the hand, however, it should be understood that a single electrode can be used to either open or close the hand depending upon the "Voluntary Open/Close" selection. The electrode type may be analog, digital, proportional, or linear.

Figure 9:
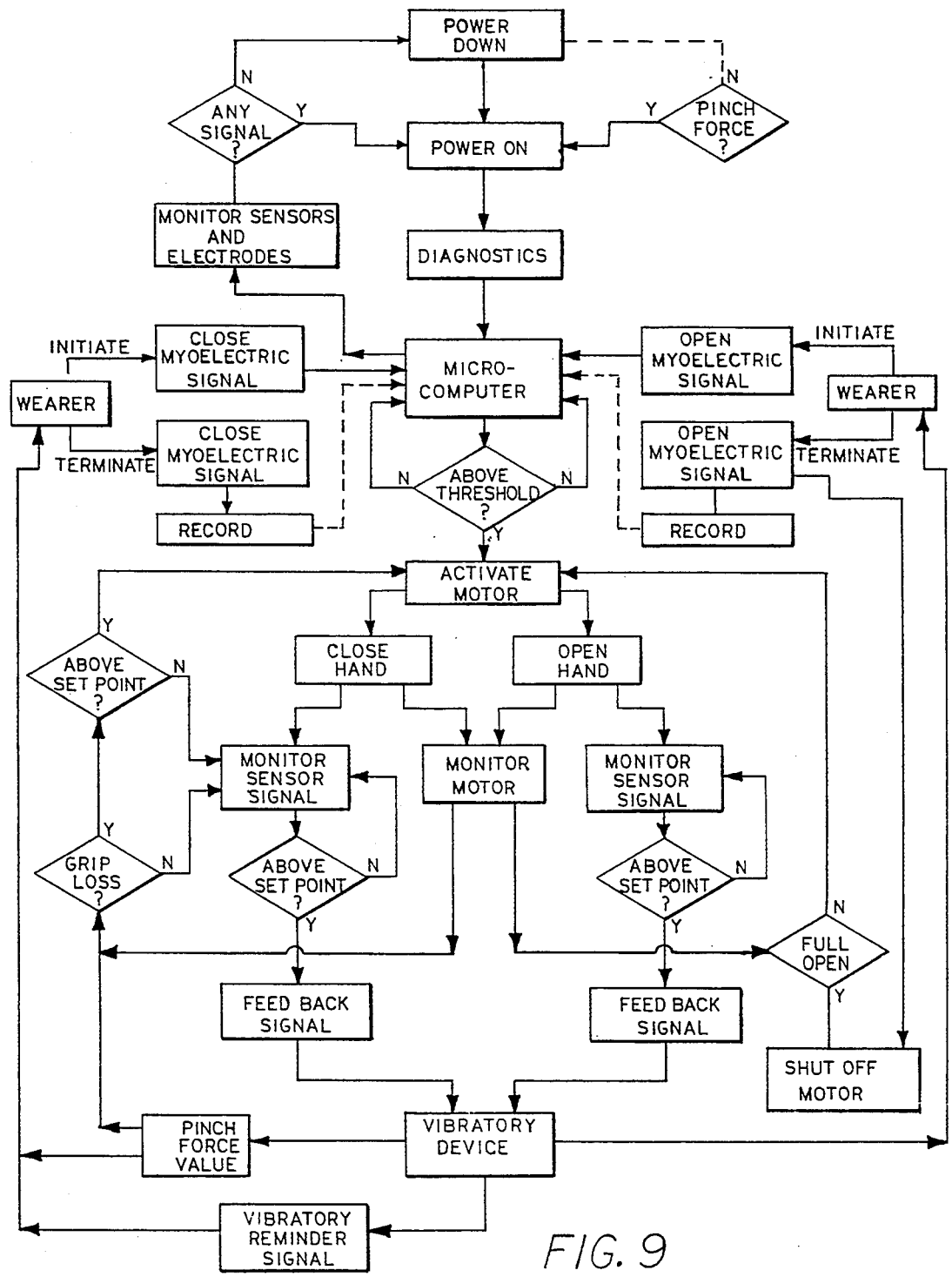
FIG. 9 is a block diagram illustrating the method of operation of the computerized electronic hand prosthesis.

Referring again to FIG. 3, and additionally to FIG. 9, the system is activated by the wearer making a decision to hold an object and flexing a muscle to activate the "hand close" electrode" 15. The "hand close" electrode 15 detects, filters, and amplifies the myoelectric signal generated by the muscle and sends the analog signal to the microcomputer 38. The microcomputer 38 then activates the motor 34 to close the hand. When the hand starts closing, regardless of where it is, a vibratory signal is immediately sent to the output vibratory device to give the wearer a reference point to start from (meaning no pressure). When the minimum force is detected on any of the fingers or thumb, another vibratory signal is sent to the output vibratory device. As the force increases, the strength of the signal increases. The feedback signal changes at various grip forces on the hand to a different vibratory pattern and amplitude.

The speed of the motor, and in turn, the closing rate of the hand is directly proportional to the intensity of the myoelectric signal generated by the wearer. The hand will continue to close as long as the myoelectric signal is present until either the hand reaches maximum pinch force or the hand travels to its mechanical stop. When either of these conditions occur, the microcomputer will immediately terminate the drive motor.

The threshold voltage points at which the microcomputer will acknowledge a valid "open" or "close" signal are each configurable. These settings can be used to eliminate nuisance activations due to movement or environmental noise. These variables are preset and stored in memory. The upper limit for "open" and "close" gain for each respective electrode can be adjusted to a lower value to allow a wearer with a weak myoelectric signal to still operate the hand at the maximum configured speed. The maximum opening and closing speeds at which the motor closes or opens the hand and the proportion to intensity are each configurable and the maximum speed at which the motor is turned on or off when the myoelectric signal goes above or below a preset threshold is also a configurable variable. These variables are preset to fit the particular wearer and are stored in memory. These features allow the system to be adjusted to match the requirements and capability of each wearer individually.

As the hand continues to close and touches an object, compression stress forces are exerted on the surfaces of the finger and thumb support members 30, 31 and 32. The strain gauge elements 35, 36, and 37 mounted on the rigid supports sense the amount of stress in the finger and thumb supports and convert it to electrical "sensor" signals. The amplitude of the electrical signal created by the strain gauges is linear and is directly proportional to the stress forces applied by the fingers and thumb. The electrical "sensor" signals created will increase as the pinching force of the fingers and thumb on the object increases.

The electrical signals created by the strain gauges is filtered and converted to a digital value by the microcomputer 38. These values are analyzed by a software program stored in memory in the microcomputer. The program in the microcomputer monitors these "pinch force" signals and when they reach a preset point, will initiate the wearer feedback. The "pinch force" is a variable which determines how much force a hand can place on an object. Typically, the hand will be set from 5 pounds of pinch force to a maximum of about 20 pounds. The "pinch force" is determined by combining the average force between the fingers and thumb with the stall current of the motor. This variable is configurable and stored in memory.

The electrical signals created by the strain gauges is converted to digital signals and is fed to the motor driven vibratory device 23 in the form of a "vibrous feedback" signal and transmitted as vibrations directly to the remnant portion of the limb for nerve stimulation. Several variables are provided for the "vibrous feedback" signal. The "Pulse Code Modulation" (PCM) can be set with the main frequency to allow maximum penetration through the skin to nerve endings and reduce the amount of power consumed. The modulation is linearly proportional to the amount of force being applied by the hand. When the minimum force is detected on any of the fingers or thumb, a vibratory signal is sent to the vibratory device 23. The pulse duration of the signal is proportional to the maximum force exerted on the fingers and thumb. As the pinch force increases, the strength and repetition of the feedback signal increases. The frequency, amplitude, and "pulse code modulation" (PCM) are adjustable and stored in memory.

The frequency of the output feedback signal can also be adjusted. It preferably is in the range of 30 cycles per second. Preliminary testing has shown that it is easier to detect minor changes on the skin surface by leaving the amplitude and base frequency at a fixed level and allow the microcomputer to vary the duty cycle of the frequency. This way the signal allows better sensitivity.

Through testing, it is possible to determine a point at which a significant "sensor" signal shift occurs. This is a point at which a force is detected on either of the fingers and the thumb indicating that the hand is gripping an object as opposed to just touching or pushing something with a finger. The range of the duty cycle will be proportional to the strength of the force applied to the fingers or thumb. The amount of frequency shift required is determined through testing. The sensor signals from the electrodes may be averaged or the dominant signal may be used.

When the command signal to close the hand is terminated by the wearer, the hand movement is halted. The microcomputer 38 records the current forces on the fingers and thumb and after a preset time delay, terminates the continuous feedback signal. Every few seconds while the wearer grips the object, the microcomputer will drive the vibratory device with an intermittent varied signal, or "vibrous reminder". To prevent the wearer from becoming numb or ignoring the feedback signal, a change in the timing and modulation of the frequency is incorporated wherein a timer turns off the vibratory feedback signal shortly after the hand stops moving and then delays for several seconds before exerting the signal again. The time delay and the modulation of the frequency change each time so as not to become repetitive and predictable. This will occur often enough to remind the wearer that the object is still being gripped, but not long enough to become monotonous or cause excessive battery drain.

If while gripping an object the microcomputer 38 detects that a force change is occurring, it will invoke the "Grip Loss Detection" (GLD) program stored in memory. The GLD monitors and analyzes the pinch force signals and determines whether the grip is being lost or just that the weight of the object is shifting. If the GLD program determines that the hand is losing the grip, it will drive the motor to close the hand in an attempt to regain the original pinch forces and grip established by the wearer. This action is independent of other wearer controlled functions. Thus, the hand can operate independently of the wearer to compensate for grip loss, however, the hand will not increase the pinch forces beyond the point set by the wearer.

A "Grip Loss Program" (GLP) stored in memory detects when there is a grip and records sensing forces. The hand is said to have a grip on an object when there is pinching force detected between the thumb and any other finger. When the hand is in the "close" mode the program detects when this condition occurs and stores the pinching forces in memory. When the hand is directed to stop closing, the final force values are recorded. The program then continuously monitors all finger forces and looks for significant changes. If the pinch force between the two fingers shifts to equal the same average value then there is no grip loss. If the force drops in the thumb and any one finger there is a grip loss. When the grip loss is detected the microcomputer immediately drives the motor in the "close" direction to re-establish the pinch forces originally set for the wearer. The time delay for activation of the "Grip Loss Detector" program and the speed of the motor 34 are configurable variables stored in memory. The motor may be driven at a speed proportional to the rate of the drop in pinch force.

A "Motor Stall Detection" program stored in memory monitors the range of voltage generated by the motor 34 and the "Back Electromotive Force" (BEMF) of the motor during the drive "off" period, linearizes the data, and interprets the forces exerted by the hand. If the generator voltage (BEMF) is near the drive voltage then the motor has very little load. If the generator voltage (BEMF) is near zero this means the motor has a large load or is stalled. The software monitors this range and by linearizing the data can interpret the force exerted by the hand.

A predetermined "Automatic Shutoff" voltage variable is stored in memory which will terminate operation of the hand to protect the batteries from extreme discharge and possible cell voltage reversal.

When the wearer is finished holding or gripping the object, he or she will flex a muscle on the "open" electrode 16 which will create a myoelectric signal to open the hand. The hand will then open to release the object and continue to open as long as the myoelectric signal is generated, or until the hand is in the fully open position where the microcomputer controller will automatically shut off the motor to save battery power.

The hand has a standby mode, or "Power Down Operation" which is invoked to minimize current consumption when there is no electrode signal or force sensor signal present. If there is no electrode signal present and no pinch force on the fingers and thumb, the microcomputer will transfer into the standby mode where the current consumption of all electronics will be approximately 10% of normal. When an electrode signal is detected, the system will immediately return to full operation. A time delay may also be incorporated before switching into a sleep mode, but the transition from sleep to active will be immediate.

A "Diagnostic" program stored in memory allows the system to perform internal diagnostics upon each "turn on", power connection, or through an external command via the communications port. A series of diagnostic tests check the status of the components and the memory devices. Any abnormalities are stored in the EEPROM for later retrieval, and may be signaled to the wearer through the motor driven vibratory device or other suitable method. Any non-fatal errors are flagged and self corrected where possible.

Any detection of abuse of the hand, (constant high levels of motor current, multiple attempts to move the hand without success, excessive force on the sensors, etc.) are logged into memory for future retrieval and analysis.

A "Security" program in memory will look for a series of events to occur. If it detects that certain events did not occur it will immediately execute a program which will write a erasure program into RAM and then proceed to erase all EPROM (set all bits to 0) and all EEPROM and write a security message in a specific memory location. Any unauthorized attempt to remove the memory contents and apply power will delete or corrupt the program. Unauthorized persons attempting to read, evaluate, or remove the system programs will only find the manufacturer's name, copyright notification, and a security message.

Figure 10:
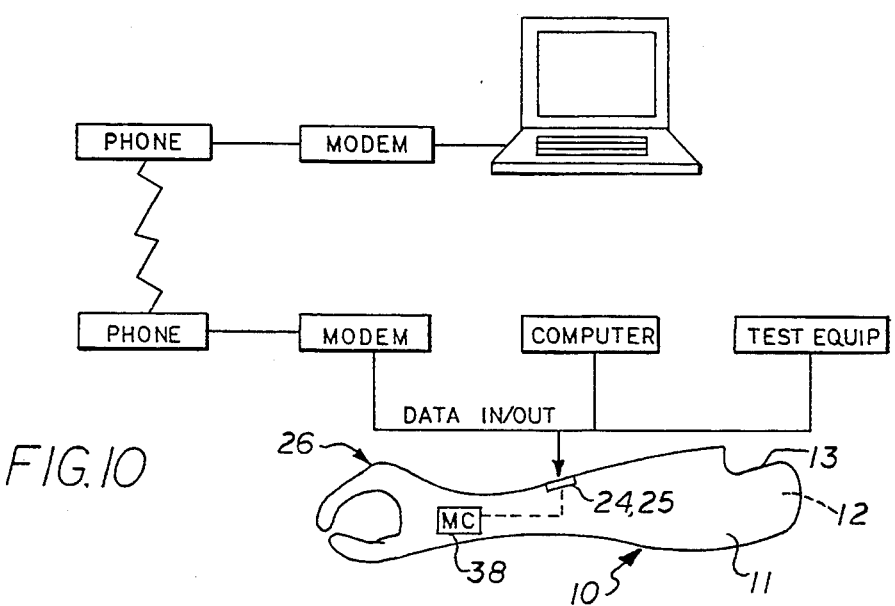
FIG. 10 is a block diagram illustrating the communication feature of the hand prosthesis.
Figure 4:
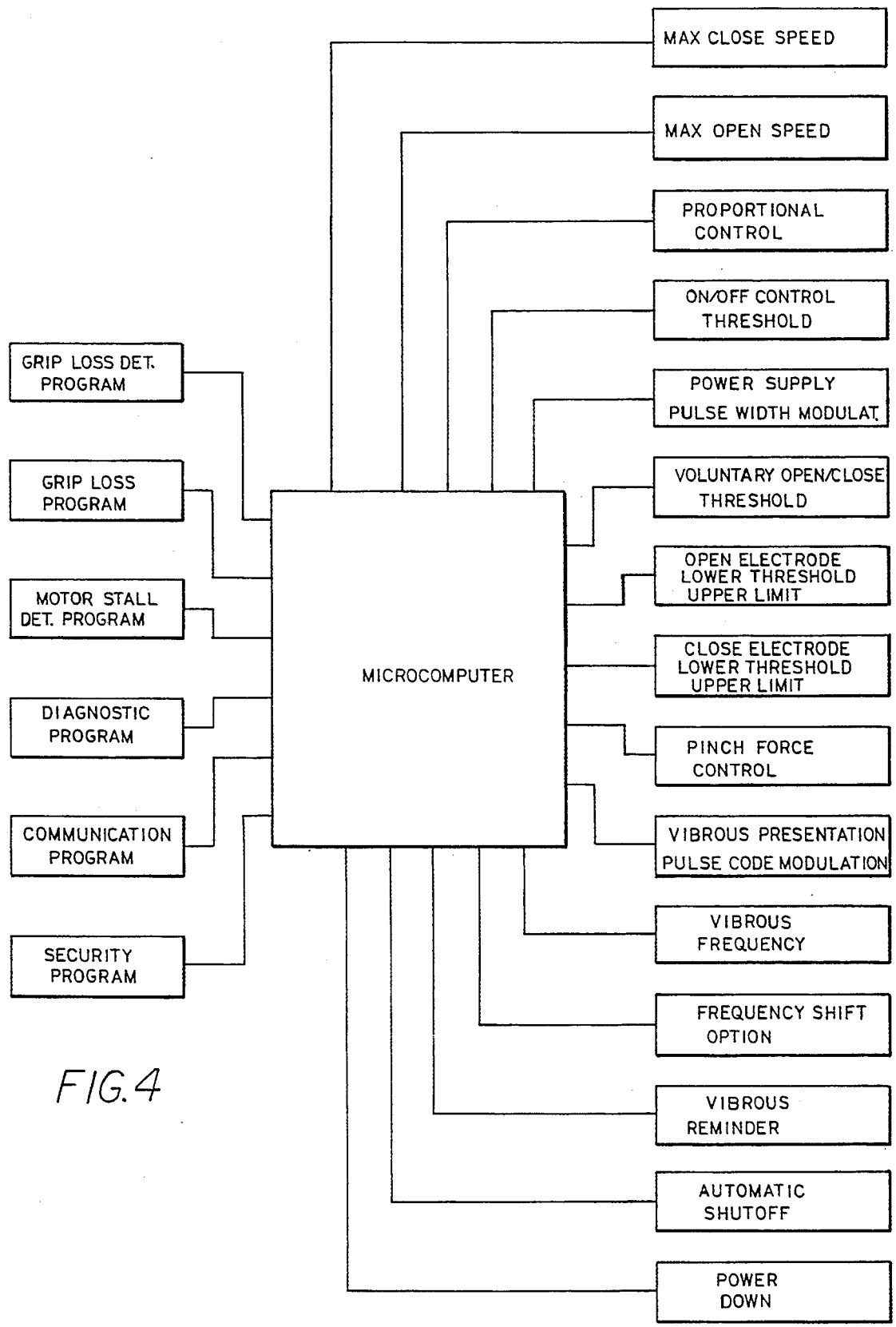
FIG. 4 is a schematic block diagram illustrating the variables, parameters, and software programs which can be changed to configure the microcomputer for hand control for a specific wearer to provide maximum wearer adaptation.
Figure 5:
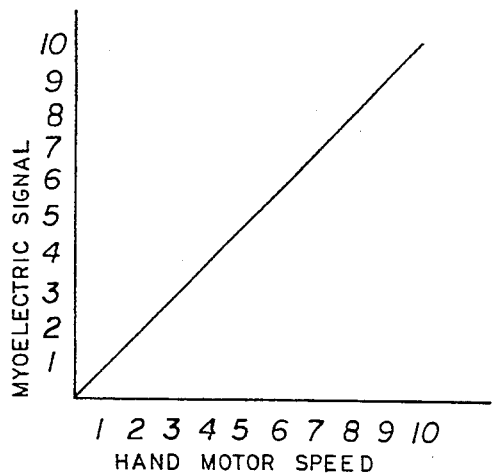
FIG. 5 is a graph illustrating the proportional control feature which allows the rate at which the hand opens or closes to be changed linearly and directly proportional to the analog signal being produced by the electrode.
Figure 6:
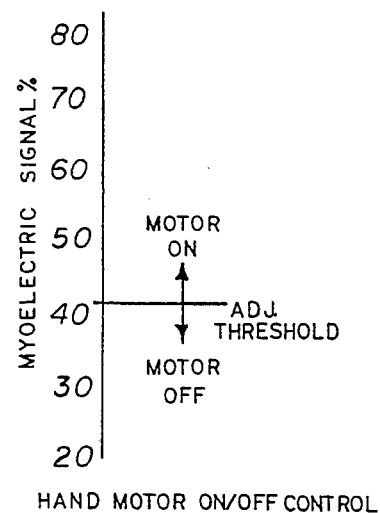
FIG. 6 is a graph illustrating the on/off mode of operation which may be varied to turn on the motor at the maximum speed when the electrode signal goes above a preset threshold and turn the motor off when the signal goes below the threshold.
Figure 7:
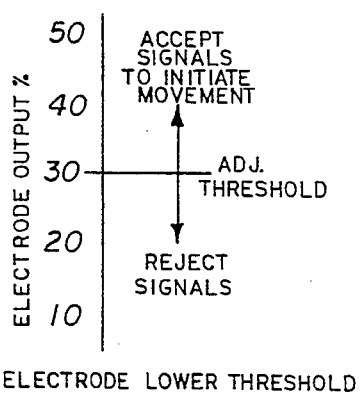
FIG. 7 is a graph illustrating the adjustable threshold voltage point at which the microcomputer will acknowledge a valid "open" or "close" signal.
Figure 8:
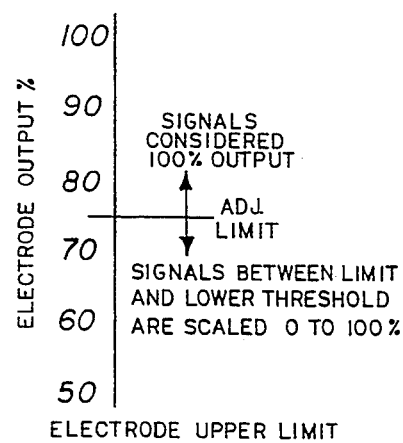
FIG. 8 is a graph illustrating the adjustable upper limit of the gain for the "open" or "close" electrode.

Referring now to FIG. 10, the communication port 24 allows the microcomputer 38 in the hand to be releasably connected to peripheral equipment, such as a modem, computer, or other equipment for exchanging data, monitoring, diagnosing, adjusting, or correcting the operational parameters of the hand. Thus, any operating problems can be diagnosed and corrected, operational data can be gathered, and operating parameters preprogrammed into the microcomputer can be easily and quickly changed through a simple telephone hookup. When a wearer receives the hand prosthesis, he also receives a small modem, a connection plug and a telephone connection. A laptop or other computer can also be connected to the communication port for initially configuring the system.

If the wearer has a problem with the hand, he can call the manufacturer of the hand prosthesis, hang up the telephone, plug the modem into the phone line, and plug the communications connector into the communication port. The manufacturer's remote computer can then call the hand via modem, and the patients hand will answer. The manufacturer can then perform diagnostic tests, determine where and if here is a problem or a battery failure and correct the problem over the phone by making corrections to the operating parameters where possible. This feature makes it possible to correct, adjust, and fine tune the gripping forces, electrode sensitivity, threshold levels, motor speed opening or closing, etc., and also periodically monitor the hand usage and operation with very little inconvenience to the wearer.

The "Security" program in memory will detect any unauthorized attempt to read, evaluate, or remove the system programs.

While this invention has been described fully and completely with special emphasis upon a preferred embodiment, it should be understood that within the scope of the appended claims the invention may be practiced otherwise than as specifically described herein.

We claim:

1. A computerized electronic prosthesis apparatus having selectively configurable operating parameters corresponding to the particular capabilities and requirements of an individual wearer comprising:

an articulated prosthesis adapted to be worn by a living being as a replacement for an amputated limb and capable of exerting a mechanical force;

programmable microcomputer means in said prosthesis connected with a power supply and including a microprocessor, memory, input/output circuitry for receiving signals and producing an output drive signal and an output vibratory signal, signal processing means, drivers, and controllers;

electrode means on said prosthesis operatively connected with said microcomputer and adapted to contact certain muscles of the remnant portion of the limb to produce an electric command signal responsive to a myoelectric signal created by the wearer contracting and relaxing certain muscles in the remnant portion, the threshold voltage points at which said microcomputer will acknowledge a valid electric command signal while eliminating nuisance activations due to movement and environmental noise selectively configured and stored in said microcomputer memory;

drive means in said prosthesis operatively connected with said microcomputer for causing said prosthesis to exert a mechanical force responsive and proportional to said electric command signal, the speed of said drive means and value of said mechanical force exerted by said prosthesis selectively configured relative to the intensity of the myoelectric signal generated by the wearer and stored in said microcomputer memory;

sensor means on said prosthesis operatively connected with said microcomputer for detecting the mechanical force exerted by said prosthesis and producing an electric sensor signal responsive and proportional thereto, the threshold voltage points at which said microcomputer will acknowledge a valid electric sensor signal selectively configured and stored in said microcomputer memory; and vibratory means on said prosthesis opperatively connected with said microcomputer and adapted to engage the remnant portion of the limb adjacent sensory nerve endings in the skin of the remnant portion of the limb and transmit vibrations which stimulate the nerve endings to produce a feedback signal perceptible to the wearer which is responsive to and indicative of the mechanical force exerted, said vibrations having frequency, amplitude, and modulation characteristics, the operating values of which are selectively configured and stored in said microcomputer memory;

upon said microcomputer receiving a valid said electric command signal, said microcomputer producing an output drive signal to operate said drive means to cause said prosthesis to exert a mechanical force relative to the intensity of the myoelectric signal generated by the wearer, and upon said microcomputer receiving a sensor signal exceeding said threshold voltage points, said microcomputer producing an output vibratory signal causing said vibratory means to transmit vibrations which stimulate the nerve endings to produce feedback signals perceptible to the wearer which are indicative of the mechanical force being exerted; and said command signal, said drive means, said sensor means, and said vibratory means each being selectively adjustable to compensate for changes in muscle strength, sensitivity, usage, and other conditions affecting operability;

a communication port on said prosthesis operatively connected with said microcomputer and adapted to be releasably connected to peripheral devices for exchanging data, monitoring, diagnosing, adjusting, correcting, or setting the operational parameters of said prosthesis; and a modem adapted for connection to a telephone and said communications port for data communication between said microcomputer in said prosthesis and a local or remote computer, whereby the wearer can call the manufacturer of said prosthesis, connect said modem into the telephone line and said communication port on said prosthesis, and the manufacturer can then communicate directly with said microcomputer in said prosthesis via telephone to perform diagnostic tests, determine where and if there is a problem or a power failure, and correct problems via the telephone by making corrections to the operating parameters of said prosthesis.

2. A computerized electronic prosthesis apparatus according to claim 1 in which
said microcomputer includes timer means,
said drive means is stopped upon the wearer relaxing a muscle which was contracted sufficiently to terminate the myoelectric signal and the mechanical force exerted by said prosthesis is maintained, and
the value of the mechanical force being exerted by said prosthesis at termination of the myoelectric signal is recorded in said microcomputer memory,
after a preset time delay said microcomputer terminates said feedback signal, and
periodically thereafter, said microcomputer drives said vibratory means to produce an intermittent reminder feedback signal perceptible to the wearer to indicate that the mechanical force is still being exerted.

3. A computerized electronic prosthesis apparatus according to claim 1 in which
said drive means is reversed upon the wearer contracting a muscle to create a myoelectric signal to produce a command signal representing the release of the exerted mechanical force,
said drive means continuing in the reversed mode as long as the myoelectric signal is created by the wearer or until said prosthesis attains a predetermined condition, and
upon termination of the myoelectric signal by the wearer or upon said prosthesis attaining a predetermined condition, said microcomputer terminating the operation of said drive means.

4. A computerized electronic prosthesis apparatus according to claim 1 in which
said prosthesis enters a standby reduced power operational mode upon said microcomputer detecting no electric command signal or no electric sensor signal to minimize current consumption of the system, and
upon detection of an electric command signal, the system immediately returning to a full power operational mode.

5. A computerized electronic prosthesis apparatus according to claim 1 in which
the upper limit value for an amount of voltage gain of said electrode means is selectively configured to facilitate maximum operation of said prosthesis by a wearer having a weak myoelectric signal and stored in said microcomputer memory.

6. A computerized electronic prosthesis apparatus according to claim 1 in which
said drive means is an electric motor and said output drive signal is selectively configured to control the speed of the motor relative to the intensity of the myoelectric signal created by the wearer and stored in said microcomputer memory.

7. A computerized electronic prosthesis apparatus according to claim 6 in which
the maximum speed at which said electric motor causes said prosthesis to exert a mechanical force is selectively configured and stored in said microcomputer memory.

8. A computerized electronic prosthesis apparatus according to claim 6 in which
proportionality of the speed at which said electric motor causes said prosthesis to exert a mechanical force relative to the intensity of the myoelectric signal created by the wearer is selectively configured and stored in said microcomputer memory.

9. A computerized electronic prosthesis apparatus according to claim 6 in which
the maximum speed at which said electric motor is turned on or off upon the myoelectric command signal going above or below the configured threshold voltage points is selectively configured and stored in said microcomputer memory.

10. A computerized electronic prosthesis apparatus according to claim 6 including
a motor stall detection program stored in said microcomputer memory which monitors and analyzes the range of voltage generated by said electric motor during a drive on mode and the back electromotive force of said electric motor during a drive off mode, linearizes the data, and interprets the data relative to the mechanical force exerted by said prosthesis.

11. A computerized electronic prosthesis apparatus according to claim 1 in which
the main frequency of said vibrations is set at a frequency to allow maximum penetration through the skin to nerve endings and reduce the amount of power consumed,
the modulation of said vibrations is linearly proportional to the electric sensor signal produced by said sensor means to represent the mechanical forces exerted by said prosthesis, and
the vibratory pattern and amplitude of said output vibratory signal being selectively configured corresponding to various mechanical force values exerted by said prosthesis and stored in said microcomputer memory, whereby
the vibratory pattern and amplitude of said output vibratory signal changes at various predetermined mechanical force values exerted by said prosthesis.

12. A computerized electronic prosthesis apparatus according to claim 1 including
a force loss detection and correction program stored in said microcomputer memory which monitors and analyzes the mechanical force being exerted by said prosthesis and upon determination that the exerted force is being reduced will activate said drive means to regain but not exceed the force originally established by said electric command signal,
the activation of said drive means to regain the force originally established being independent of myoelectric signals created by the wearer, such that
said prosthesis is capable of automatically detecting and compensating for loss of mechanical force without any action on the part of the wearer.

13. A computerized electronic prosthesis apparatus according to claim 1 including
a diagnostics program stored in said microcomputer memory and invoked upon power being supplied at start up which performs internal diagnostic tests to check the status and condition of the operating components and memory devices, record any detected abnormalities in memory for later retrieval, and to correct any abnormalities where possible.

14. A computerized electronic prosthesis apparatus according to claim 1 including a security program stored in said microcomputer memory which monitors and detects any unauthorized attempt to read, evaluate, or remove the system programs, and upon detection thereof to provide only the manufacturer's name, copyright notification, and a security message.

15. A method of controlling the operation of an electronic prosthesis apparatus relative to the particular capabilities and requirements of a particular wearer and providing feedback signals to the wearer relative to the prosthesis operation comprising the steps of:

providing an articulated prosthesis to be worn by a living being as a replacement for an amputated limb and capable of exerting a mechanical force, said prosthesis including programmable microcomputer means connected with a power supply and having a microprocessor, memory, input/output circuitry for receiving signals and producing an output drive signal and an output vibratory signal, signal processing means, drivers, and controllers;

providing electrode means on said prosthesis operatively connected with said microcomputer which contact certain muscles of the remnant portion of the limb to produce an electric command signal responsive to a myoelectric signal created by the wearer contracting and relaxing certain muscles in the remnant portion;

setting threshold voltage points at which said microcomputer will acknowledge a valid electric command signal while eliminating nuisance activations due to movement or environmental noise and storing the setting in said microcomputer memory;

providing drive means in said prosthesis operatively connected with said microcomputer for causing said prosthesis to exert a mechanical force responsive and proportional to said electric command signal;

setting the speed of said drive means and the value of said mechanical force exerted by said prosthesis relative to the intensity of the myoelectric signal generated by the wearer and storing the setting in said microcomputer memory;

providing sensor means on said prosthesis operatively connected with said microcomputer for detecting the mechanical force exerted by said prosthesis and producing an electric sensor signal responsive and proportional thereto;

setting the threshold voltage points at which said microcomputer will acknowledge a valid electric sensor signal and storing the setting in said microcomputer memory;

providing vibratory means on said prosthesis operatively connected with said microcomputer and adapted to engage the remnant portion of the limb adjacent sensory nerve endings in the skin of the remnant portion and transmit vibrations having frequency, amplitude, and modulation characteristics which stimulate the nerve endings to produce a feedback signal perceptible to the wearer which is responsive to and indicative of the mechanical force exerted;

setting the operating values of the frequency, amplitude, and modulation characteristics of said vibrations and storing the operating values in said microcomputer memory;

configuring said microcomputer to receive said electric command signal and, responsive to a valid electric command signal, to produce an output drive signal to operate said drive means to cause said prosthesis to exert a mechanical force relative to the intensity of the myoelectric signal generated by the wearer;

configuring said microcomputer to receive and monitor said sensor signal and upon said sensor signal exceeding said threshold voltage points to produce an output vibratory signal to cause said vibratory means to transmit vibrations such that upon said microcomputer receiving a valid said electric command signal, said microcomputer produces an output drive signal to operate said drive means to cause said prosthesis to exert a mechanical force relative to the intensity of the myoelectric signal generated by the wearer, and upon said microcomputer receiving a sensor signal exceeding said threshold voltage points, said microcomputer produces an output vibratory signal causing said vibratory means to transmit vibrations which stimulate the nerve endings to produce feedback signals perceptible to the wearer which are indicative of the mechanical force being exerted;

providing a communication port on said prosthesis operatively connected with said microcomputer and adapted to be releasably connected to peripheral devices for exchanging data, monitoring, diagnosing, adjusting, correcting, or setting the operational parameters of said prosthesis;

providing for a modem adapted for connection to a telephone and said communications port for data communication between said microcomputer in said prosthesis and a local or remote computer, whereby the wearer can call the manufacturer of said prosthesis, connect said modem into the telephone line and said communication port on said prosthesis, and the manufacturer can then communicate directly with said microcomputer in said prosthesis via telephone to perform diagnostic tests, determine where and if there is a problem or a power failure, and correct problems via the telephone by making corrections to the operating parameters of said prosthesis.

16. The method according to claim 15 including the steps of:

providing a communication port on said prosthesis operatively connected with said microcomputer; and releasably connecting said communication port to peripheral devices, and exchanging data, monitoring, diagnosing, adjusting, correcting, and setting the operational parameters of said prosthesis as necessary to facilitate maximum operation of said prosthesis.

17. The method according to claim 15 including the steps of:

setting the upper limit value for an amount of voltage gain of said electrode means to facilitate maximum operation of said prosthesis by a wearer having a weak myoelectric signal and storing the setting in said microcomputer memory.

18. The method according to claim 15 in which said drive means is an electric motor, and including the step of;

setting said output drive signal to control the speed of the motor relative to the intensity of the myoelectric signal created by the wearer and storing the setting in said microcomputer memory.

19. The method according to claim 18 including the step of;
    setting the maximum speed at which said electric motor causes said prosthesis to exert a mechanical force and storing the setting in said microcomputer memory.

20. The method according to claim 18 including the step of;
    setting the proportionality of the speed at which said electric motor causes said prosthesis to exert a mechanical force relative to the intensity of the myoelectric signal created by the wearer and storing the setting in said microcomputer memory.

21. The method according to claim 12 including the steps of;
    setting the maximum speed at which said electric motor is turned on or off upon the electric command signal going above or below the set threshold voltage points and storing the setting in microcomputer memory.

22. The method according to claim 16 including the steps of;
    electronically monitoring and analyzing the range of voltage generated by said electric motor during a drive on mode and the back electromotive force of said electric motor during a drive off mode, linearizing the data, and interpreting the data relative to the mechanical force exerted by said prosthesis 23. The method according to claim 15 in which
    the main frequency of said vibrations is set at a frequency to allow maximum penetration through the skin to nerve endings and reduce the amount of power consumed,
    the modulation of said vibrations is set to be linearly proportional to the electric sensor signal produced by said sensor means to represent the mechanical forces exerted by said prosthesis, and
    the vibratory pattern and amplitude of the output vibratory signal is set at predetermined values corresponding to various mechanical force values such that as the mechanical force exerted by the prosthesis changes, the vibratory pattern and amplitude of said vibrations change corresponding to the set mechanical force values.

24. The method according to claim 15 including the step of
    electronically monitoring and analyzing the mechanical force being exerted by said prosthesis and, upon determination that the exerted force is being reduced, activating said drive means to regain but not exceed the force originally established by said electric command signal,
    the activation of said drive means to regain the force originally established being independent of myoelectric signals created by the wearer, such that
    said prosthesis is capable of automatically detecting and compensating for loss of mechanical force without any action on the part of the wearer.

25. The method according to claim 15 including the steps of
    storing a diagnostics program in said microcomputer memory, and
    invoking said diagnostics program upon power being supplied at start up to perform internal diagnostic tests to check the status and condition of the operating components and memory devices, record any detected abnormalities in memory for later retrieval, and to correct any abnormalities where possible.

26. The method according to claim 15 including the steps of
    storing a security program in said microcomputer memory,
    invoking said security program upon power being supplied at start up, and
    electronically monitoring and detecting any unauthorized attempt to read, evaluate, or remove the system programs, and upon detection thereof causing said microcomputer to provide only find the manufacturer's name, copyright notification, and a security message.

* * * * *